United States Patent [19]

Levine et al.

[11] Patent Number: 5,382,510
[45] Date of Patent: Jan. 17, 1995

[54] METHODS OF DIAGNOSING PRE-CANCER OR CANCER STATES USING PROBES FOR DETECTING MUTANT P53

[75] Inventors: Arnold J. Levine; Thomas E. Shenk, both of Princeton, N.J.; Cathy A. Finlay, Yardley, Pa.

[73] Assignee: The Trustees of Princeton University, Princeton, N.J.

[21] Appl. No.: 912,011

[22] Filed: Jul. 10, 1992

Related U.S. Application Data

[63] Continuation of Ser. No. 543,963, Jun. 27, 1990, abandoned.

[51] Int. Cl.$^6$ .............................................. C12Q 1/68
[52] U.S. Cl. ..................................... 435/6; 435/91.1; 435/91.2; 436/501; 436/508; 436/513; 436/547; 436/548; 436/63; 436/64
[58] Field of Search ..................... 435/6, 7.1, 91, 91.1, 435/91.2; 436/501, 508, 513, 547, 548, 63, 64, 94, 811, 813

[56] References Cited

U.S. PATENT DOCUMENTS

| | | | |
|---|---|---|---|
| 4,762,706 | 8/1988 | McCormick et al. | |
| 4,786,718 | 11/1988 | Weinberg et al. | |
| 4,798,787 | 1/1989 | McCormick et al. | 435/7 |
| 4,871,838 | 10/1989 | Bos et al. | 536/27 |

OTHER PUBLICATIONS

Zakut-Houri et al. (1985) Embo J., vol. 4, No. 5, pp. 1251–1255.
Baker et al. Science, 244, 217–221 (1989).
Finlay et al, Molecular and Cellular Biology 8, 531–539 (1988).
Clarke et al, Molecular and Cellular Biology 8, 1206–1215 (1988).
Tan et al, Journal of Virology 59, 574–583 (1988).
Hinds et al, Molecular and Cellular Biology 7, 2863–2869 (1987).
Hinds et al, Journal of Virology 63, 739–746 (1989).
Hinds et al, "The P53 Proto-Oncogene Can Suppress Transformation by Other Oncogenes, and Mutations in The Proto-Oncogene Can activate the Gene for Transformation," in Common Mechanisms of Transformation by Small DNA Tumor Viruses, Luis P. Villarreal, American Society For Microbiology, Chaper 7 (1989).
Levine et al, "The P53 Proto-Oncogene And Its Product", In Common Mechanisms Of Transformation By Small DNA Tumor Viruses, Villarreal, ed., American Society For Microbiology (1989).
Finlay et al, Cell 57, 1083–1093 (1989).
Frey et al, Journal of Virology 63, 5440–5444 (1989).
Werness et al, Science 248 76–79 (1990).
Levine, BioEssays, contains a review of tumor suppressor genes, including p53.
Gannon et al, EMBO J. 9, 1595–1602 (1990).
Nigro et al, Nature 342, 705–708 (1990).
Baker et al, Science 244, 217–221 (1989).
Harlow et al, Molecular and Cellular Biology 5, 1601–1610 (1985).
Bressac et al, Proc. Natl. Acad. Sci. USA 87, 1973–1977 (1990).
A news item Laboratory Diagnostics.
Iggo et al, The Lancet 335, 675–679 (1990).
Takahashi et al, Science 246, 491–494 (1989).

*Primary Examiner*—Margaret Parr
*Assistant Examiner*—Ardin H. Marschel
*Attorney, Agent, or Firm*—Irving N. Feit; Laura S. Weiss

[57] ABSTRACT

A panel of probes that detect and distinguish between sets of human p53 gene or protein mutations that frequently occur or are selected for in pre-cancer and cancer cells, each set giving rise to a phenotype that is different from that of wild-type p53 and of at least one other set of p53 mutants.

6 Claims, No Drawings

METHODS OF DIAGNOSING PRE-CANCER OR CANCER STATES USING PROBES FOR DETECTING MUTANT P53

This is a continuation of Ser. No. 543,963, filed Jun. 27, 1990, abandoned, the contents of which are incorporated in their entirety herein.

The present invention is directed to the use of molecular probes in the detection of cancer and pre-cancer states. More specifically, the invention is directed to distinguishing between different cancer and pre-cancer states by means of antibody and DNA probes. The cancer and pre-cancer states are those associated with the p53 protein.

Mutations of proto-oncogenes in somatic cells are increasingly being recognized as significant in the induction of human cancers. Some examples of oncogenes formed by such mutations include: neu, fes, fos, myc, myb, fms, Ha-ras, and Ki-ras. The mutations that convert proto-oncogenes to oncogenes are often point mutations. Much needs to be learned in order to understand how oncogenes and their expression products function to transform normal cells to cancer cells.

Oncogenes are generally believed to act in a dominant fashion. This is generally considered to mean that the conversion of a proto-oncogene to an oncogene results in the acquisition of a new function, i.e., enhancing transformation.

A different type of mutation associated with cancer occurs when a tumor suppressor gene is altered in a way that causes the product of the gene to lose its tumor suppressor function. An example of such a tumor suppressor gene is the retinoblastoma sensitivity gene, Rb. Tumor suppressor genes are sometimes called recessive oncogenes, although, strictly speaking, the products of tumor suppressor genes do not contribute to tumor formation. The phenotype is recessive since, when both alleles are mutated, the absence of a tumor suppressor gene results in an enhancement of tumorigenesis.

The products of certain viral oncogenes are also able to transform cells. Examples of such products include the E6 and E7 proteins from human papilloma virus, the large T antigen from SV40, and E1a from adenovirus. Viral oncogene proteins are believed to bind to and, thereby, to inactivate tumor suppressor proteins, such as the retinoblastoma protein.

A gene product that exhibits some properties of both a dominant and a recessive oncogene is the 53 kd phosphoprotein, p53. Evidence is growing that mutations in the p53 gene are associated with a large number of many types of cancers. For example, Iggo et al, Lancet 335, 675–679 (1990) has expressed the opinion that p53 is the most common proto-oncogene to undergo mutation in lung cancers.

Much of what is known about p53 has been derived from studying the effect of transfecting wild-type and mutant murine p53 in rat embryo fibroblast cells. This work has been reviewed by Levine et al, "The P53 Proto-Oncogene And Its Product," in *Common Mechanisms Of Transformation By Small DNA Tumor Viruses*, L. Villarreal, ed., American Society for Microbiology, Chapter 2 (1989); Hinds et al, ibid, Chapter 7; and Levine, BioEssays 12, 60–66 (1990).

Briefly, a number of point mutations between amino acids 130 and 240 of p53 (out of 390 amino acids) lead to significant, tumor-promoting changes in phenotype. Both wild-type and mutant p53 are often found at increased levels in transformed cells due to an increase in their metabolic stabilities. The stabilization of mutant p53 is believed to occur through the formation of a complex with cellular proteins, such as the 70 kd heat shock protein, hsc70. The stabilization of wild-type p53 is believed to be associated with its ability to form a complex with the mutant p53-hsc70 complex. These results are consistent with the proposition that alterations in p53 function are involved in the process of cellular transformation. The involvement of mutant murine p53 in the transformation of cells in culture is also apparent from the ability of mutant, but not wild-type, p53 to cooperate with activated Ha-ras to transform primary rat embryo cells.

The p53 gene resides on chromosome 17p. Many cancers, such as those discussed above, are associated with chromosome 17p deletions. Such allelic deletions often indicate the presence of a tumor suppressor gene. The mutation of one allele gives rise to a benign, pre-cancer state. The mutation of the second allele gives rise to the malignant cancer state.

Finlay et al, Cell 57, 1083–1093 (1989), has presented further evidence that wild-type murine p53 displays properties of a suppressor of transformation. Three observations are consistent with this theory.

First, the introduction of wild-type murine p53 into primary rodent cells, along with two cooperating transforming genes, ras and E1a, results in a decrease in the number of transformed foci. The transformed cell lines that were obtained were found to contain the murine p53 gene, but either failed to express it or produced high levels of an altered murine product. Thus, overexpression of the wild-type murine p53 protein appears to be detrimental to the process of transformation of cultured rat cells by oncogenes.

Second, inactivation of the p53 gene is believed to be associated with the development of Friend virus-induced erythroleukemia in mice (Mowat et al, Nature 314, 633–636 (1985)). There are numerous examples in the literature of tumor cells derived from the spleens of mice infected with the Friend virus complex containing rearrangements or other mutations at the p53 gene locus; see, for example, Ben-David, Oncogene 3, 179–185 (1988).

The third line of evidence consistent with the possibility that the wild-type p53 protein is a member of a group of proteins involved in suppression of transformation is the ability, mentioned above, of p53 to form oligomeric protein complexes with viral oncogenes, such as the SV40 large T antigen, the adenovirus type 5 E1b-55 kd protein, and the human papilloma virus (HPV) type 16 or 18 E6 product; see, for example, Werness, Science 248, 76–79 (1990). Analogous complexes have also been observed between p105, the product of the retinoblastoma susceptibility gene, and the SV40 large T antigen (DeCaprio et al, Cell 54, 275–283 (1988)); the adenovirus E1a protein (Whyte et al, Nature 334, 124–129 (1988)); and the E7 protein of HPV-16 or -18 (Muenger et al, EMBO J. 8, 4099–4105 (1989)).

These interactions between viral proteins and p105 are thought to inactivate a growth-suppressive function of p105, thus mimicking deletions and mutations commonly found in the retinoblastoma gene in tumor cells. Similarly, oligomeric protein complex formation between these same viral proteins and p53 may eliminate or alter the growth-suppressive function of p53; see Finlay et al, id.

The clonal nature of p53-related tumors is consistent with a tumor progression model in which non-neoplastic pre-cancer cells bearing a wild-type p53 gene and a mutated p53 gene have a distinct proliferative advantage over normal cells, which contain two wild-type genes. The advantage is due to mutant p53-mediated interference with wild-type p53 function. The increased proliferative capacity of such non-neoplastic cells increases the probability of a second, inactivating mutation, i.e., gene conversion or deletion, at the p53 locus. The resulting cells, which now contain mutations in both p53 alleles, are able to express the fully neoplastic phenotype; see Finlay et al, id., and Baker et al, Science 244, 217–221 (1989).

The above model is supported by the discovery that human tumor cells from which a 17p chromosome allele been deleted contain mutations in the remaining allele. The mutations tended to be clustered in four "hot spots," which coincided with the four most highly conserved regions of the p53 gene; see Nigro et al, Nature 342, 705–708 (1989).

Gannon et al, EMBO J. 9, 1595–1602 (1990), propose that all human mutant p53 proteins are recognized by a monoclonal antibody, PAb240. These authors suggest that all p53 mutants exert a common conformational effect, which results in expression of the PAb240 epitope.

OBSERVATIONS OF THE INVENTORS THAT FORM THE BASIS OF THE PRESENT INVENTION

Previously unpublished experiments of the inventors relating to human p53 form the basis of the present invention. Different human p53 clones isolated from colorectal carcinomas possess mutations at amino acid residues 143, 175, 273 or 281 (out of a total of 393 residues). Such p53 mutants, when co-transfected into rat embryo fibroblasts (REFs) with activated wild-type ras oncogenes, cooperate with the oncogenes to transform the REFs in culture. All of the transformed cell lines derived from these experiments produce the human p53 protein in elevated levels.

The mutations are summarized in Table 1. The effect of the mutations on properties of human p53 mutant protein is shown in Table 2.

TABLE 1

Mutations of Human p53 Protein

| Clone | DNA Nucleotide | DNA Alteration | Protein Residue | Protein Alteration |
|---|---|---|---|---|
| p53-c143A | 428 | T → C | 143 | val → ala |
| p53-175H | 524 | G → A | 175 | arg → his |
| p53-273H | 818 | G → A | 273 | arg → his |
| p53-281G | 842 | A → G | 281 | asp → gly |

TABLE 2

Properties of Human p53 Mutant Proteins

| Clone | Relative TX Frequency | Half-life Protein | hsc Bound | p90 Bound | Tumors in Nude Mice |
|---|---|---|---|---|---|
| p53-cWT[1] | 0 | 20 min. | − | + | + |
| p53-c143A[1] | 1.6 | 1.5–2 hrs. | + | + | + |
| p53-WT[2] | 0 | ND[3] | ND[3] | ND[3] | ND[3] |
| p53-175H[2] | 11.5 | 3.6–6.4 hrs. | + | + | + |
| p53-273H[2] | 4.7 | 7 hrs. | − | + | + |
| p53-281G[2] | 1.9 | 3.5 hrs.[4] | − | + | ND[3] |

[1] cDNA. Does not contain introns.
[2] contains introns.
[3] Not Determined
[4] half-life estimated in cell lines expressing ras + E1a + mutant p53

In order to obtain the results shown in Table 2, cDNA clones or partial cDNA-genomic clones of p53, plus the activated ras oncogene, were co-transfected into primary rat embryo fibroblasts. In each set of transfections, transformed foci were scored two to three weeks later in duplicate cell cultures.

The results in Table 2 demonstrate that mutant human p53 cDNA or cDNA-genomic hybrid clones derived from colon carcinomas can behave as dominant oncogenes and cooperate with the ras oncogene in transforming rat embryo fibroblasts. Four different missense mutations, at amino acids residues 143, 175, 273 and 281, each contributed to the transformed phenotype. In all these cases, the human p53 mutant protein was produced in high levels in the transformed cell at least in part due to the extended half-life of these mutant proteins.

Unexpectedly, the phenotypes of cells containing the different mutants are not the same. For example, the three p53 DNA clones containing "hot spot" mutations, i.e. p53-175H, p53-273H, and p53-281G, have characteristic and reproducible transformation frequencies (number of foci produced) in a ratio of 6:2.4:1, indicating that these "hot spot" mutations are not equivalent in their phenotypes.

More striking is the fact that p53-175H and p53-c143A mutant proteins bind to hsc70 in transformed cells while the p53-273H and p53-281G mutant proteins do not detectably interact with or bind to hsc70. Previous experiments have shown that some mutant murine p53 proteins have an altered conformation (Hinds et al, Mol. Cell. Biol. 7, 2863–2869 (1987); Finlay et al, Ibid. 8, 531–539 (1988)). It is possible that such altered p53 molecules bind to hsc70 and sequester wild-type p53 in a complex that blocks proper folding, assembly or localization of p53. Thus, p53-c143A and p53-175H may represent mutant proteins which never fold correctly and thus retain their affinity for hsc70. If wild-type p53 is recruited into this complex, the p53-mutant-hsc70-p53-wild-type complex would poison the function of wild-type p53.

This cannot be the case for the p53-273H and p53-281G mutants; which, as mentioned above, do not bind to hsc70. The p53-273H human mutant protein can associate with the rat p53 protein and form an oligomeric complex as demonstrated by co-immunoprecipitation with a human-specific antibody, Ab-2. This complex is not mediated by hsc70 and may be less efficient in sequestering the rat cellular wild-type p53 protein. This is consistent with a poorer ability to transform cells in culture.

In contrast to co-transfections with activated ras plus mutant human p53, co-transfections with activated ras plus wild-type human p53 resulted in a very low frequency of focus formation, and only one focus could be cloned into an established cell line. Thus, it appears likely that mutation of human p53 activates a dominant transforming function that is not detectable in wild-type p53.

In summary, it now appears that all of the human p53 mutant proteins differ from the wild-type human p53 protein by having an extended half-life, by being expressed at higher levels, and by possessing the ability to transform cells in culture. These data support the suggestion that mutation of p53 on one allele could have a growth-promoting phenotype in vivo, which expands the number of cells with such mutations and favors the selection of a second mutational event (deletion or gene conversion) in the cancer cells. The observation that many tumor cells retain only the mutant p53 allele suggests that these mutant proteins are not fully dominant over the wild-type allele, or that the mutants continue to confer a proliferative advantage on cells in the absence of wild-type p53. Such a positive effect of mutant p53 on cell proliferation in the absence of wild-type p53 could be an intrinsic function of the molecule, or could be mediated by titration of cellular proteins other than endogenous p53, for example, via the protein p90.

Most significantly, the results establish that there are classes of human p53 mutations that give rise to pre-cancer and cancer cells with different phenotypes. It is apparent that these different phenotypes can give rise to cancers that take different courses and have different prognoses.

A problem with present methods to detect cancer is that these different phenotypic changes have not been taken into account. This problem is addressed by the present invention.

A second problem addressed by the present invention is to determine how the different phenotypic changes affect the course and prognosis of cancer. Once this problem has been solved, a further problem is to be able to detect the various phenotypic changes in order to be able to predict the course a cancer will take and the best way to treat such cancer.

SUMMARY OF THE INVENTION

These and other problems as will be apparent to those having ordinary skill in the art have been solved by providing a panel of probes that detect and distinguish between sets of human p53 gene or protein mutations that frequently occur or are selected for in pre-cancer and cancer cells, each set giving rise to a phenotype that is different from that of wild-type p53 and of at least one other set of p53 mutants.

The invention further relates to a method of distinguishing between sets of human p53 gene or protein mutations that are frequently occurring or selected for in pre-cancer or cancer cells, each set giving rise to a phenotype that is different from the wild-type gene or protein and from at least one other set of mutations, the method comprising determining the mutations in a sample of p53 genes or proteins with a panel of probes that detect and distinguish between such sets.

The invention also provides a method of distinguishing between sets of human p53 protein mutations that are frequently occurring or selected for in pre-cancer or cancer cells, the method comprising the steps of determining whether such a mutation exists and, if so, whether the mutant protein binds to hsc70 less tightly than wild-type human p53 protein.

DETAILED DESCRIPTION OF THE INVENTION

The present invention is directed to the detection of mutations in wild-type p53 genes and proteins. For the purposes of the present specification, the term "wild-type" p53 means the nucleotide or amino acid sequence reported by Matlashewski et al, EMBO J. 13, 3257–3262 (1984); Zakut-Houri et al, EMBO J. 4, 1251–1255 (1985) (SEQ ID NO: 1); and Lamb and Crawford, Mol. Cell. Biol. 5, 1379–1385 (1986). The sequences are available from GenBank. Wild-type p53 includes a proline/arginine polymorphism at amino acid 72 and the corresponding nucleotide polymorphism.

The detection of mutations in wild-type p53 genes and proteins is important, since such mutations indicate pre-cancer and cancer states. There are no apparent limitations in regard to the type of cancer that is associated with a p53 mutation. Such cancer include, generally, colorectal, lung, ovarian, cervical, adrenal cortex, bone, bladder, breast, brain, and mesenchyme cancers and, more specifically, chronic myelocytic leukemia, chronic myelogenous leukemia, and osteogenic sarcomas.

A pre-cancer cell is defined as a cell that has one normal p53 allele and one mutated p53 allele. The mutation is usually a point mutation.

In a cancer cell, both alleles are mutated. One mutation is usually a point mutation, as described above for a pre-cancer cell. The other mutation is usually a deletion of all or a significant part of the p53 gene.

The invention is based on the unexpected discovery that there are sets of mutations that correspond to sets of different conformations and different phenotypes. It is important to determine as many sets of mutations as possible. It is not, however, necessary to determine each individual mutation within a set. A set of mutations is defined as having at least one mutation and giving rise to a phenotype that is different from the wild type and at least one other set of mutations.

Each set of phenotypes leads to a distinguishable course and severity of the same disease. Therefore, by determining sets of mutations, a physician can not only determine that a patient has a particular cancer, but can distinguish different subsets of prognoses and prescribe the best treatment.

For example, many colorectal cancers give rise to mutations at amino acid positions 143, 175, 273 and 281. These mutations are described in Table 1.

One set of mutations comprises mutations at amino acids 143 and 175. A second set of mutations comprises mutations at amino acids 273 and 281. Therefore, a panel of probes in accordance with the invention includes at least two members. There may be as many as three, four five or six sets of mutations and, therefore, the same number of probes.

The mutations in a set are commonly found in various types of human tumors. The ubiquitous nature of these mutations may result from their frequent occurrence or, as explained above, because they provide a proliferative advantage to cells containing them and, therefore, are selected for.

Alterations in either the nucleotide sequence of the gene or the amino acid sequence of the protein may be assayed in order to determine whether a mutation within one of the sets of mutations in accordance with the present invention exists. Alterations in the amino acid sequence may be probed by antibodies. Alterations in the nucleotide sequence may be probed by means of nucleotide probes or, in some cases, by restriction endonucleases. Nucleotides as used herein refer to RNA or DNA.

An "antibody" in accordance with the present specification is defined broadly as a polypeptide that binds specifically to an epitope. The antibody may be polyclonal or monoclonal. Antibodies further include recombinant polyclonal or monoclonal Fab fragments prepared in accordance with the method of Huse et al, Science 246, 1275–1281 (1989).

Methods for preparing polyclonal and monoclonal antibodies that exhibit specificity toward single amino acid differences between oncogenes are described by McCormick et al in U.S. Pat. No. 4,798,787. These methods are incorporated herein by reference.

Briefly, polyclonal antibodies may be produced by injecting a host mammal, such as a rabbit, mouse, rat, or goat, with the p53 protein or a fragment thereof capable of producing antibodies that distinguish between mutant p53 and wild-type p53. The peptide or peptide fragment injected may contain the wild-type sequence or the mutant sequence. Sera from the mammal are extracted and screened to obtain polyclonal antibodies that are specific to the peptide or peptide fragment.

In order to produce monoclonal antibodies, a host mammal is inoculated with a peptide or peptide fragment as described above, and then boosted. Spleens are collected from inoculated mammals a few days after the final boost. Cell suspensions from the spleens are fused with a tumor cell in accordance with the general method described by Kohler and Milstein in Nature 256, 495–497 (1975). In order to be useful, a peptide fragment must contain sufficient amino acid residues to define the epitope of the p53 molecule being detected.

If the fragment is too short to be immunogenic, it may be conjugated to a carrier molecule. Some suitable carrier molecules include keyhold limpet hemocyanin and bovine serum albumen. Conjugation may be carried out by methods known in the art. One such method is to combine a cysteine residue of the fragment with a cysteine residue on the carrier molecule.

The peptide fragments may be synthesized by methods known in the art. Some suitable methods are described by Stuart and Young in "Solid Phase Peptide Synthesis," Second Edition, Pierce Chemical Company (1984).

A variety of assays are available for detecting proteins with labelled antibodies. Such methods may involve one step or two steps. In a one-step assay, the target p53 molecule, if it is present, is immobilized and incubated with a labelled antibody. The labelled antibody binds to the immobilized p53. After washing to remove unbound molecules, the sample is assayed for the presence of the label.

In a two-step assay, immobilized p53 is incubated with an unlabelled antibody. The p53-unlabelled antibody complex, if present, is then bound to a second, labelled antibody that is specific for the unlabelled antibody. The sample is washed and assayed for the presence of the label, as described above.

The label may be a radioactive atom, an enzyme, or a chromophoric moiety. Some examples of radioactive atoms include $P^{32}$, $I^{125}$, $H^3$, and $C^{14}$. Some examples of enzymes include horseradish peroxidase, alkaline phosphatase, beta-galactosidase, and glucose-6-phosphate dehydrogenase. Some examples of chromophoric moieties include fluorescein and rhodamine. The antibodies may be conjugated to these labels by methods known in the art. For example, enzymes and chromophoric molecules may be conjugated to the antibodies by means of coupling agents, such as dialdehydes, carbodiimides, dimaleimides, and the like. Alternatively, conjugation may occur through a ligand-receptor pair. Some suitable ligand-receptor pairs include, for example, biotin-avadin or -streptavadin, and antibody-antigen.

The probes of the present invention may also be oligonucleotides that distinguish wild-type from mutant DNA or RNA. The oligonucleotide probes may be prepared by methods known in the art. Suitable methods for synthesizing oligonucleotide probes are described by Caruthers in Science 230, 281–285 (1985).

The oligonucleotide probes may contain a sequence complementary to a sequence of wild-type or mutant p53 that comprises a nucleotide involved in a mutation. For example, the nucleotide involved in a mutation may be that at position 428, 524, 818, or 842 of wild-type or mutant p53.

The length of the oligonucleotide probe is not critical, as long as it is capable of hybridizing to a test sample containing wild-type or mutant p53 and distinguishing between the two. The oligonucleotide should contain at least 6 nucleotides, preferably at least 10 nucleotides, and, more preferably, at least 15 nucleotides.

There is no upper limit to the length of the oligonucleotide probes. Longer probes are more difficult to prepare and require longer hybridization times. Therefore, the probe should not be longer than necessary. Normally, the oligonucleotide probe will not contain more than 50 nucleotides, preferably not more than 40 nucleotides, and, more preferably, not more than 30 nucleotides.

Methods for distinguishing wild-type oncogenes from mutants containing a single nucleotide change are described in PCT Application WO 87/07646. These methods are incorporated herein by reference.

Briefly, oligonucleotides containing either the wild-type or mutant sequence are hybridized under stringent conditions to dried agarose gels containing target p53 RNA or DNA digested with an appropriate restriction endonuclease. Suitable stringent conditions include two degrees below the calculated $T_m$ of a perfect duplex. The oligonucleotide probe hybridizes to the target p53 detectably better when the probe and the target p53 are perfectly complementary.

The target p53 DNA is optionally amplified in order to improve the sensitivity of the assay. Amplification may be accomplished by methods known in the art. A suitable method is the polymerase chain reaction method, as described in Mullis et al, U.S. Pat. Nos. 4,683,195 and 4,683,202.

A particularly convenient method for assaying a single point mutation by means of oligonucleotides is described in Segev, PCT Application WO 90/01069, licensed to ImClone Systems Incorporated, New York City. This method is limited to cases wherein the nucleotide in wild type p53 that is mutated and the corresponding nucleotide in the mutant are not complementary.

Briefly, two oligonucleotide probes for each wild-type or mutated p53 strand being assayed are prepared. Each oligonucleotide probe is complementary to a sequence that straddles the nucleotide that either becomes or has been mutated. Thus, a gap is created between the two hybridized probes.

For example, in order to distinguish between wild type and mutant forms of p53, wherein the guanine at position 524 in the wild type form is mutated to adenine, probes that leave a gap at position 524 are prepared. The gap is filled with a mixture of a polymerase, a ligase, and the nucleotide complementary to that at position 524 to form a ligated oligonucleotide product. For example, if wild-type p53 is being detected, the gap is filled with cytosine. The mutant form will not be detected under these conditions.

On the other hand, if the mutant form is being detected, the gap will be filled with thymine. The wild-type p53 will not be detected under these conditions. Either of the oligonucleotides or the nucleotide filling the gap may be labelled by methods known in the art.

The ligated oligonucleotide product can be amplified by denaturing it from the p53, hybridizing it to additional oligonucleotide complement pairs, and filling the gap again, this time with the complement of the nucleotide that filled the gap in the first step.

To illustrate the method, structure (1) shows a pair of oligonucleotide probes hybridizing to wild-type p53 containing guanine at position 526. Structure (2) shows the gap between the two probes being filled with cytosine. Structure (3) shows the ligated oligonucleotide product from structure (2) hybridizing to two additional complementary oligonucleotides. Structure (4) shows the gap in Structure (3) being filled with guanine. This process can be repeated as often as is desired.

STRUCTURES

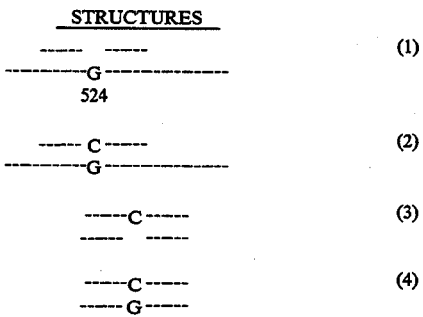

Following ligation of a ligated oligonucleotide product and, optionally, amplification, the oligonucleotide product is separated by size and the label is detected by methods known in the art. The description of the above procedure from PCT Application WO 90/01069 is incorporated herein by reference.

Mutations may also be detected if they create or abolish restriction sites. For example, the Hha I site is GCGC. The mutation in the human p53 gene at nucleotide 428 from thymine to cytosine creates an Hha I site. Such a mutation alters the amino acid sequence at residue 143 from valine to alanine; see Table 1.

A mutation of the human p53 gene at nucleotide 524 from guanine to adenine abolishes an Hha I site. Such a mutation causes an alteration at residue 175 from arginine to histidine; see Table 1.

Accordingly, the mutations indicated in Table 1 at residues 428 and 524 of the human p53 gene may be detected by restriction analysis; see Baker et al, Science 244, 217-221 (1989). Some additional examples of the use of restriction analysis to assay point mutations is given in Weinberg et al, U.S. Pat. No. 4,786,718.

Some additional methods for distinguishing polynucleotide sequences differing by one nucleotide are described by De Ley et al, J. Bacteriol. 101, 738-754 (1970); Wood et al, Proc. Natl. Acad. USA 82, 1585-1588 (1985); Myers et al, Nature 313, 495-497 (1985); and Myers et al, Science 230, 1242-1246 (1985). These methods are incorporated herein by reference.

The labels that can be conjugated to oligonucleotide probes for detection are the same as those that are conjugated to antibodies. Such labels are described above. Conjugating the labels to the oligonucleotides is achieved by methods known in the art.

The labeled probes described above are capable of distinguishing wild-type and sets of mutant forms of p53. Confirmation may be obtained by comparing the response of the probes to the different forms. The wild-type p53 gene and protein are known, and may be obtained by known methods, such as those described in Matlashewski et al, EMBO J. 13, 3257-3262 (1984); Zakut-Houri et al, EMBO J. 4, 1251-1255 (1985); and Lamb and Crawford, Mol. Cell. Biol. 5, 1379-1385 (1986). Mutants may be prepared from wild-type p53 by site-directed mutagenesis; see, for example, Zoller and Smith, Nucl. Acids Res. 10, 6487-6500 (1982); Methods in Enzymology 100, 468-500 (1983); and DNA 3, 479-488 (1984).

Wild-type and mutant p53 structural genes may also be synthesized by known methods, such as by preparing overlapping double-stranded oligonucleotides, filling in the gaps, and ligating the ends together. The DNA may be cloned in a suitable host cell and expressed. The p53 DNA and protein may be recovered from the host cell. See, generally, Sambrook et al, "Molecular Cloning," Second Edition, Cold Spring Harbor Laboratory Press (1987).

Assays involving antibody and DNA probes are conducted in accordance with methods known in the art. The assay may be designed so that the probes test positive for wild-type p53 and negative for mutant p53. In such a case, it is preferable to use an oligonucleotide probe, which will not be affected by the specific mutation.

On the other hand, the probes may test positive for mutant p53 and negative for wild-type p53. In such a case, it is preferable to use antibodies, which detect protein. The preference for antibody probes is due to the presence of higher concentrations of mutant p53 protein than wild-type p53 protein in transformed cells.

It has unexpectedly been found that at least one set of human p53 mutants does not detectably bind to the heat shock protein hsc70 or, at least, binds significantly less tightly than wild-type p53. This set comprises mutations at amino acid positions 273 and 281. Therefore, this set may be distinguished from the other sets of mutants, such as the set that comprises mutations at amino acid positions 143 and 175, by determining whether any mutation exists and, if so, whether the mutants bind to hsc70. Methods for

SEQUENCE LISTING ( 1 ) GENERAL INFORMATION:

(i i i) NUMBER OF SEQUENCES: 1

(2) INFORMATION FOR SEQ ID NO:1:

(i) SEQUENCE CHARACTERISTICS:
  (A) LENGTH: 1317 base pairs
  (B) TYPE: nucleic acid
  (C) STRANDEDNESS: single
  (D) TOPOLOGY: linear (i i) MOLECULE TYPE: cDNA (x i) SEQUENCE DESCRIPTION: SEQ ID NO:1:

| | | | | | | |
|---|---|---|---|---|---|---|
| GTCTAGAGCC | ACCGTCCAGG | GAGCAGGTAG | CTGCTGGGCT | CCGGGGACAC | TTTGCGTTCG | 60 |
| GGCTGGGAGC | GTGCTTTCCA | CGACGGTGAC | ACGCTTCCCT | GGATTGGCAG | CCAGACTGCC | 120 |
| TTCCGGGTCA | CTGCCATGGA | GGAGCCGCAG | TCAGATCCTA | GCGTCGAGCC | CCCTCTGAGT | 180 |
| CAGGAAACAT | TTTCAGACCT | ATGGAAACTA | CTTCCTGAAA | ACAACGTTCT | GTCCCCCTTG | 240 |
| CCGTCCCAAG | CAATGGATGA | TTTGATGCTG | TCCCCGGACG | ATATTGAACA | ATGGTTCACT | 300 |
| GAAGACCCAG | GTCCAGATGA | AGCTCCCAGA | ATGCCAGAGG | CTGCTCCCCC | CGTGGCCCCT | 360 |
| GCACCAGCAG | CTCCTACACC | GGCGGCCCCT | GCACCAGCCC | CCTCCTGGCC | CCTGTCATCT | 420 |
| TCTGTCCCTT | CCCAGAAAAC | CTACCAGGGC | AGCTACGGTT | TCCGTCTGGG | CTTCTTGCAT | 480 |
| TCTGGGACAG | CCAAGTCTGT | GACTTGCACG | TACTCCCCTG | CCCTCAACAA | GATGTTTTGC | 540 |
| CAACTGGCCA | AGACCTGCCC | TGTGCAGCTG | TGGGTTGATT | CCACACCCCC | GCCCGGCACC | 600 |
| CGCGTCCGCG | CCATGGCCAT | CTACAAGCAG | TCACAGCACA | TGACGGAGGT | TGTGAGGCGC | 660 |
| TGCCCCACC | ATGAGCGCTG | CTCAGATAGC | GATGGTCTGG | CCCCTCCTCA | GCATCTTATC | 720 |
| CGAGTGGAAG | GAAATTTGCG | TGTGGAGTAT | TTGGATGACA | GAAACACTTT | TCGACATAGT | 780 |
| GTGGTGGTGC | CCTATGAGCC | GCCTGAGGTT | GGCTCTGACT | GTACCACCAT | CCACTACAAC | 840 |
| TACATGTGTA | ACAGTTCCTG | CATGGGCGGC | ATGAACCGGA | GGCCCATCCT | CACCATCATC | 900 |
| ACACTGGAAG | ACTCCAGTGG | TAATCTACTG | GGACGGAACA | GCTTTGAGGT | GCGTGTTTGT | 960 |
| GCCTGTCCTG | GGAGAGACCG | GCGCACAGAG | GAAGAGAATC | TCCGCAAGAA | AGGGGAGCCT | 1020 |
| CACCACGAGC | TGCCCCCAGG | GAGCACTAAG | CGAGCACTGC | CAACAACAC | CAGCTCCTCT | 1080 |
| CCCCAGCCAA | AGAAGAAACC | ACTGGATGGA | GAATATTTCA | CCCTTCAGAT | CCGTGGGCGT | 1140 |
| GAGCGCTTCG | AGATGTTCCG | AGAGCTGAAT | GAGGCCTTGG | AACTCAAGGA | TGCCCAGGCT | 1200 |
| GGGAAGGAGC | CAGGGGGGAG | CAGGGCTCAC | TCCAGCCACC | TGAAGTCCAA | AAAGGGTCAG | 1260 |
| TCTACCTCCC | GCCATAAAAA | ACTCATGTTC | AAGACAGAAG | GGCCTGACTC | AGACTGA | 1317 | determining relative binding affinities may be conducted by methods known in the art. For example, a method for determining whether a p53 protein binds to hsc70 is described by Finlay et al in Mol. and Cell. Biol. 8, 531–539 (1988) and by Hinds et al in Mol. and Cell. Biol., 7, 2863–2869 (1987). The method described in these papers, which is incorporated herein by reference, involves co-immunoprecipitation experiments with anti-p53 and anti-hsc70 antibodies.

A suitable antibody specific for hsc70, for example, may be prepared from the sera of rabbits immunized with the carboxy-terminal 21 amino acids of a 70kd heat shock protein family member, hsp70, as described in the Hinds et al article, Id. The method of preparing the antibody as described in the Hinds et al article is incorporated herein by reference.

What we claim is:

1. A method of correlating a set of human p53 gene or protein point mutations in pre-cancer or cancer cells with a phenotype, the method comprising:
 (a) determining which set of human p53 gene or protein mutations point is present in a sample of pre-cancer or cancer cells with a probe or probes that can distinguish between sets of human p53 gene or protein point mutations, each set of point mutations correlating with a phenotype that is different from the phenotype associated with the wild-type p53 gene or protein and from the phenotype associated with at least one other set of point mutations; and
 (b) correlating the set of gene or protein point mutations with its transformation frequency, half-life, or ability to bind to the heat shock protein hsc70, or a phenotype related thereto.

2. A method according to claim 1 wherein one set of mutations comprises a mutation at amino acid position 143 or 175 of the p53 protein or at codon 143 or 175 of a DNA molecule encoding the p53 protein.

3. A method according to claim 1 wherein one set of mutations comprises a mutation at amino acid position 273 or 281 of the p53 protein or at codon 273 or 281 of a DNA molecule encoding the p53 protein.

4. A method according to claim 1 wherein the probes are antibodies.

5. A method according to claim 1 wherein the probes are DNA probes.

6. A method according to claim 4 wherein the antibodies are monoclonal.

* * * * *

UNITED STATES PATENT AND TRADEMARK OFFICE
CERTIFICATE OF CORRECTION

PATENT NO. : 5,382,510
DATED : January 17, 1995
INVENTOR(S) : Arnold J. Levine, et al.

It is certified that error appears in the above-indentified patent and that said Letters Patent is hereby corrected as shown below:

Column 1, line 8, insert

--The U.S. government has a paid-up license in this invention and the right in limited circumstances to require the patent owner to license others on reasonable terms as provided for by the terms of grant no. 5 P01 CA 41086 awarded by the National Institute of Health.--

Signed and Sealed this

Second Day of November, 1999

Attest:

Q. TODD DICKINSON

*Attesting Officer*    *Acting Commissioner of Patents and Trademarks*